US00PP10700P

United States Patent [19]

Ilsink

[11] Patent Number: Plant 10,700

[45] Date of Patent: Nov. 24, 1998

[54] FLORIBUNDA ROSE PLANT NAMED 'INTERBAB'

[75] Inventor: G. P. Ilsink, JA Doorn, Netherlands

[73] Assignee: DeVor Nurseries, Inc., Watsonville, Calif.

[21] Appl. No.: 804,657

[22] Filed: Feb. 25, 1997

[51] Int. Cl.[6] ..... A01H 5/00

[52] U.S. Cl. ..... Plt./24

[58] Field of Search ..... Plt./24

[56] References Cited

PUBLICATIONS

UPOV–RUM, Plant Variety Database, 1997/03, GTI Jouve Retrieval software, cites ES PBR 011000381, NL PBR R001966, and DE PBR ROS 01277 ('Interbab').

*Primary Examiner*—Howard J. Locker
*Attorney, Agent, or Firm*—Christie, Parker & Hale, LLP

[57] ABSTRACT

A floribunda rose variety producing yellow flowers.

1 Drawing Sheet

BACKGROUND OF THE INVENTION

The present invention relates to a new and distinct floribunda rose variety which was originated by my crossing an undistributed seedling as seed and as pollen parent the variety known as 'Carte d 'Or.' The varietal denomination of this new rose is 'Interbab'.

SUMMARY OF THE INVENTION

Among the novel characteristics possessed by the new variety which distinguish it from its parents and all other varieties of which I am aware are its attractive, yellow flowers borne in sprays on a bushy, vigorous plant.

Asexual reproduction by budding of the new variety as performed in Watsonville, Calif., shows that the foregoing and other distinguishing characteristics come true to form and are established and transmitted through succeeding propagations. Other known forms of asexual reproduction for roses, may be also employed.

Comparison with Parents

The new variety differs from the female parent by, among other characteristics, in producing flower sprays with longer and stronger stems and from the male parent by having smaller flowers, different flower color and more flower spray production.

BRIEF DESCRIPTION OF ILLUSTRATION

The accompanying illustration show typical specimens of the vegetative growth and flowers of the new variety in different stages of development and depicted in color as nearly true as it is reasonably possible to make the same in a color illustration of this character.

BRIEF DESCRIPTION OF THE NEW VARIETY

Parentage: Seedling.
*Seed parent.*—'Seedling'.
*Pollen parent.*—'Carte d'Or'.
Class: Floribunda.

The following is a detailed description of the new variety, form specimens grown outdooors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Flower

Blooming habit: Continuous.

A. Bud:
- (1) *Size.*—Small.
- (2) *Form.*—Pointed.
- (3) *Color.*—When sepals first divide, bud color is near 22D to 19B.
- (4 ) *Sepals.*—Foliaceous, about 1.7 to 2 cm in length, longer than bud, sepals are upright then reflex at maturity. Color: Near 144A.
- (5 ) *Peduncle.*—Length: About 4 cm to about 6 cm. Aspect: Rough. Strength: Slender. Color: Near 144A.
- (6) *Bracts.*—About 2 or 3, narrow, lanceolate, near 137A, about 3 cm below calyx.

B. Bloom:
- (1 ) *Size.*—Average size when fully expanded — about 4 cm to about 5 cm.
- (2) *Borne.*—Clusters of about 5 to 8 blooms.
- (3) *Form.*—Imbricated, petal edges curling under slightly.
- (4) *Petalage.*—Number of petals under normal conditions — about 23 to 30 .
- (5) *Color* (⅓–½ *open*).—Outer petals — Top surface: Near 8D to 9C. Undersurface: Near 8D to 9C. Inner Petals — Top surface: Near 16D. Undersurface: Near 16D. Base of petals: Near 9B. General tonality from a distance: Pale Yellow.
- (6) *Color* (*Fully open*).—Outer petals — Top surface: Tip: Near 8D to 9C; rest of petal is near 8C. Undersurface: Tip: Near 8D; rest of petal is near 8C. Inner petals — Top surface: Near 15D. Undersurface: Near 15D. Base of petals: Near 9B. General tonality from a distance: Golden Yellow.
- (7) *Color change.*—Color changes from a pale yellow color to a more golden yellow. Petal top surface: Yellow-orange 15D. Petal undersurface: Yellow-orange 15D. Base of petals: Yellow-group 9B. General tonality at a distance: Golden yellow.

C. Petals:
- (1) *Texture.*—Thick, slightly veiny.
- (2) *Appearance.*—Inside matte, and outside matte.
- (3) *Form.*—Fan-shaped with pointed apex.
- (4) *Arrangement.*—Imbricated.

(5) *Petaloids.*—Few, about 1 to 5.
(6)*Persistence.*—Petals drop off cleanly.
(7) *Fragrance.*—Slight fruity fragrance.
(8) *Lasting quality.*—On plant about 10 to 14 days; about 8 to 10 days after cutting.

Reproductive Organs

A. Stamens:
(1) *Arrangement.*—Regularly arranged around styles.
(2) *Stamens.*—Anthers: Color — near 17B. Filaments: Color — near 5B.
(3) *Pollen.*—Color — near 17B.
B. Pistils:
(1) *Styles.*—Bunched, about 0.05 cm above stigma.
(2) *Stigmas.*—Color — near 1C.
Characteristics of hips: Not observed.

Plant

A. Form: Short, compact, upright.
B. Growth: Vigorous.
C. Foliage: Compound 3 to 7 leaflets.
(1) *Size.*—Small.
(2) *Quantity.*—Abundant.
(3) *Color.*—New foliage — upper side near 147A underside near 147B, mature foliage — upper side near 147A, underside near 147B.
(4) *Shape.*—Oval.
(5) *Texture.*—Upper side slight gloss; underside matte, veiny.
(6) *Edge.*—Serrate.
(7) *Serration.*—Denticulate.
(8) *Leaf stem.*—Color — medium green.
(9) *Stipules.*—Long, very slightly curved outward, slightly bearded.
(10) *Rachis.*—Small prickles underneath.
(11) *Petioles.*—Top near 137A, underside near 146B.
(12) *Auricle.*—Short, bearded margins, curving outward slightly.
(13) *Resistance to disease.*—Good resistance to mildew, rust and blackspot.
D. Wood:
(1) *New wood.*—Color near 144A, bark smooth.
(2) *Old wood.*—Color near 146A, bark smooth.
E. Flower stem: About 35 cm to about 46 cm from last cut.
F. Thorns:
(1) *Thorns.*—Quantity: Few on basals and laterals; thin, straight wing-shaped, about 0.05 cm, near 150D, irregular.
G. Winter hardiness: Winter hardy in Watsonville, Calif.

I claim

1. A new and distinct variety of floribunda rose plant, substantialy as shown and described.

* * * * *

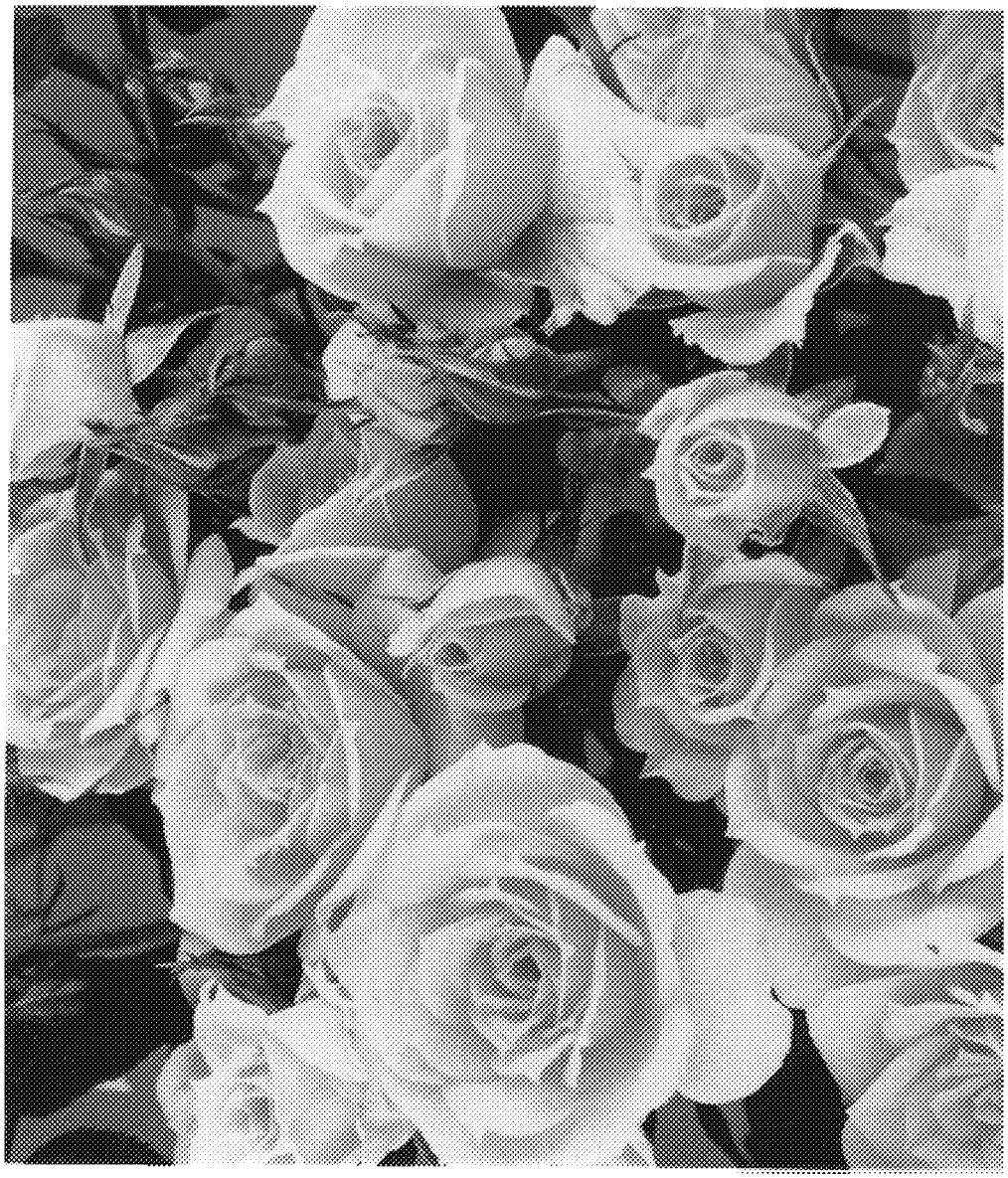

UNITED STATES PATENT AND TRADEMARK OFFICE

CERTIFICATE OF CORRECTION

PATENT NO. : Plant 10,700
DATED : November 24, 1998
INVENTOR(S) : G. P. Ilsink

It is certified that error appears in the above-identified patent and that said Letters Patent is hereby corrected as shown below:

Column 1, line 44, replace "form" with -- from --.
Column 3, line 17, before "Characteristics" insert -- C. --.
Column 4, line 27, replace "substantialy" with -- substantially --.

Signed and Sealed this

Eighth Day of February, 2000

*Attest:*

*Attesting Officer*

Q. TODD DICKINSON

*Commissioner of Patents and Trademarks*